(12) United States Patent
Kojima et al.

(10) Patent No.: US 8,080,623 B2
(45) Date of Patent: Dec. 20, 2011

(54) POLYMERIZABLE COMPOSITION, CROSSLINKABLE RESIN, AND MANUFACTURE METHODS AND APPLICATIONS THEREOF

(75) Inventors: Kiyoshige Kojima, Tokyo (JP); Junji Kodemura, Tokyo (JP)

(73) Assignee: Zeon Corporation, Tokyo (JP)

( * ) Notice: Subject to any disclaimer, the term of this patent is extended or adjusted under 35 U.S.C. 154(b) by 354 days.

(21) Appl. No.: 12/446,126

(22) PCT Filed: Oct. 19, 2007

(86) PCT No.: PCT/JP2007/070409
§ 371 (c)(1),
(2), (4) Date: Apr. 17, 2009

(87) PCT Pub. No.: WO2008/047895
PCT Pub. Date: Apr. 24, 2008

(65) Prior Publication Data
US 2011/0144292 A1  Jun. 16, 2011

(30) Foreign Application Priority Data

Oct. 20, 2006 (JP) ................. 2006-285811
Oct. 30, 2006 (JP) ................. 2006-293847

(51) Int. Cl.
C08G 61/08 (2006.01)
C08F 2/02 (2006.01)
B32B 15/08 (2006.01)
C08F 4/70 (2006.01)

(52) U.S. Cl. ........ 526/281; 526/227; 526/282; 526/283; 526/327; 526/902; 427/385.5; 156/307.3

(58) Field of Classification Search .................. 526/281, 526/283, 327, 902, 227, 282; 427/385.5; 156/307.3
See application file for complete search history.

(56) References Cited

U.S. PATENT DOCUMENTS

2006/0211834 A1  9/2006  Sugawara
2009/0305018 A1  12/2009 Ohtaki et al.

FOREIGN PATENT DOCUMENTS

| | | |
|---|---|---|
| EP | 1990364 A1 | 11/2008 |
| EP | 2067812 A1 | 6/2009 |
| JP | 2001-226466 A | 8/2001 |
| JP | 2002-265573 A | 9/2002 |
| WO | WO 97/03096 * | 1/1997 |
| WO | WO-2004/003052 A1 | 1/2004 |
| WO | WO-2007/091551 A1 | 8/2007 |

* cited by examiner

*Primary Examiner* — Fred M Teskin
(74) *Attorney, Agent, or Firm* — Birch, Stewart, Kolasch & Birch, LLP

(57) ABSTRACT

A polymerizable composition suitable as an electric material and the like used in an electric circuit board, which comprises a norbornene monomer, a metathesis polymerization catalyst, and a chain transfer agent composed of a compound represented by formula (A):

$$CH_2=CH-Y-OCO-CR^1=CH_2$$

wherein Y represents a divalent hydrocarbon group having 3 to 20 carbon atoms, and $R^1$ represents a hydrogen atom or a methyl group. By further comprising a crosslinking agent in the polymerizable composition, obtaining a crosslinkable resin by carrying out bulk polymerization, and crosslinking the crosslinkable resin to obtain a molded article and a crosslinked resin composite having excellent characteristics such as electric insulation, adhesion, mechanical strength, heat resistance, dielectric properties and the like.

18 Claims, No Drawings

POLYMERIZABLE COMPOSITION, CROSSLINKABLE RESIN, AND MANUFACTURE METHODS AND APPLICATIONS THEREOF

TECHNICAL FIELD

The present invention relates to a polymerizable composition, a crosslinkable resin, and manufacture methods and applications thereof. More particularly, the present invention relates to a polymerizable composition from which a crosslinkable resin can be obtained that is suitable as an electric material and the like used in an electric circuit board, a crosslinkable resin obtained using such polymerizable composition, and a method for manufacturing the crosslinkable resin, and applications of a crosslinked body, a composite and the like being excellent in electric insulation, adhesion, mechanical strength, heat resistance, dielectric properties and the like.

BACKGROUND ART

It is known that a crosslinked molded product can be obtained by crosslinking a thermoplastic norbornene resin, which is obtained by ring-opening metathesis polymerization of a norbornene monomer, with a crosslinking agent such as an organic peroxide. For example, Patent Literature 1 discloses a method in which an organic peroxide and a crosslinking aid are added to a thermoplastic hydrogenated ring-opening norbornene resin, the resultant mixture is homogeneously dispersed to obtain a norbornene resin composition, this composition is molded into a film or a prepreg, this film or prepreg is laminated on a substrate, and then the resultant laminate is crosslinked and fused by heat-press molding to obtain a crosslinked molded product. Patent Literature 1 discloses that the crosslinked molded product is useful as an interlayer insulation film, a film for forming a moisture-proof layer and the like.

Patent Literature 1: Japanese Patent Laid-Open No. 6-248164

Patent Literature 2 discloses a method in which a norbornene monomer is metathesis-polymerized in the presence of a ruthenium carbene complex, which is a metathesis polymerization catalyst, and a crosslinking agent, and then post-cured (post-crosslinked). Patent Literature 2 teaches that a highly densely crosslinked polymer can be obtained by this method.

Patent Literature 2: International Publication No. WO 97/03096

Further, Patent Literature 3 discloses that a composite material was obtained by carrying out bulk polymerization of a polymerizable composition which comprises a norbornene monomer, a metathesis polymerization catalyst, a chain transfer agent, and a crosslinking agent to obtain a crosslinkable thermoplastic resin, and then laminating this crosslinkable thermoplastic resin on a substrate or the like and crosslinking the laminated resin.

Patent Literature 3: International Publication No. WO 2004/003052

Further, Patent Literature 4 discloses a method of manufacturing a macromonomer which, in carrying out ring-opening metathesis polymerization, uses a metathesis polymerizable monomer, a metathesis polymerization catalyst, and an allyl compound such as an allyl alcohol, an allyl isocyanate, an allyl isothiocyanate, an allylamine, and an allyl acrylate.

Patent Literature 4: Japanese Patent Laid-Open No. 2001-226466

DISCLOSURE OF THE INVENTION

Problems to be Resolved by the Invention

According to researches made by the present inventors, a composite in which a crosslinked body and a substrate are laminated, obtained by the method disclosed in the above-described Patent Literatures, has low adhesion between the crosslinked body and the substrate in some cases because of difficulty of embedding of the crosslinked body into bumps on the substrate surface. Further, the composite has large dielectric loss at a 1 GHz frequency in some cases, so that the composite was limitedly applied to a high frequency circuit board.

Objects of the present invention are to provide a polymerizable composition from which a crosslinkable resin can be obtained that is suitable as an electric material and the like used in an electric circuit board, a crosslinkable resin obtained using such polymerizable composition, a method for manufacturing the crosslinkable resin and so on, and applications as a crosslinked body, a composite and the like being excellent in electric insulation, adhesion, mechanical strength, heat resistance, dielectric properties and the like.

Means of Solving the Problems

The inventors earnestly proceeded with studies in order to achieve the above objects and found that a crosslinked body being excellent in electric insulation, adhesion, mechanical strength, heat resistance, dielectric properties and the like, can be obtained by, in a polymerizable composition comprising a norbornene monomer, a metathesis polymerization catalyst, and a chain transfer agent, using a long chain compound having a vinyl group and an acryloyl group or a methacryloyl group as the chain transfer agent. Based on this knowledge, further studies were made, whereby the present invention was completed.

Specifically, the present invention includes the following embodiments.

(1) A polymerizable composition comprising a norbornene monomer, a metathesis polymerization catalyst, and a chain transfer agent composed of a compound represented by formula (A):

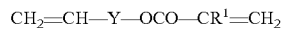

$$CH_2=CH-Y-OCO-CR^1=CH_2$$

wherein Y represents a divalent hydrocarbon group having 3 to 20 carbon atoms, and $R^1$ represents a hydrogen atom or a methyl group.

(2) The above polymerizable composition, further comprising a crosslinking agent.

(3) A crosslinkable resin obtainable by bulk polymerization of the above polymerizable composition.

(4) The above crosslinkable resin, wherein molecular weight distribution (Mw/Mn) represented by a ratio (Mw/Mn) of weight average molecular weight (Mw) to number average molecular weight (Mn) is 3 or less.

(5) The above crosslinkable resin, wherein the residual amount of the chain transfer agent is 5% or less of the added amount thereof.

(6) A crosslinkable resin composite obtainable by coating or impregnating the above polymerizable composition onto or into a support, and then carrying out bulk polymerization.

(7) A crosslinked body formable by crosslinking the above crosslinkable resin.

(8) A crosslinked resin composite formable by crosslinking a molded article of the above crosslinkable resin on a support.

(9) A crosslinked resin composite formable by crosslinking the above crosslinkable resin composite.

(10) The above crosslinked resin composite, wherein the crosslinking is carried out on an added support.

(11) A method of manufacturing a crosslinkable resin, comprising the step of carrying out bulk polymerization of the above polymerizable composition.

(12) A method of manufacturing a crosslinkable resin composite, comprising the steps of coating or impregnating the above polymerizable composition onto or into a support, and then carrying out bulk polymerization of the polymerizable composition.

(13) A method of manufacturing a crosslinked body, comprising the step of crosslinking the above crosslinkable resin.

(14) A method of manufacturing a crosslinked resin composite, comprising the step of crosslinking a molded article of the above crosslinkable resin on a support.

(15) A method of manufacturing a crosslinked resin composite, comprising the step of crosslinking the above crosslinkable resin composite.

(16) The above method of manufacturing a crosslinked resin composite, wherein the crosslinking is carried out on an added support.

Advantages of the Invention

The polymerizable composition of the present invention is subjected to bulk polymerization and then crosslinked to obtain a crosslinked body being excellent in electric insulation, adhesion, mechanical strength, heat resistance, dielectric properties and the like.

Laminating the crosslinked body on a film-like substrate or compositing the crosslinked body with a fiber material can give a composite body having the above-described characteristics.

The crosslinked body and composite obtained using the polymerizable composition of the present invention are suitable as an electric material used in an electric circuit board, and the like.

BEST MODE FOR CARRYING OUT THE INVENTION

[Polymerizable Composition]

The polymerizable composition in the present invention comprises a norbornene monomer, a metathesis polymerization catalyst, and a chain transfer agent composed of a compound represented by the formula (A).

(1) Norbornene Monomer

The norbornene monomer composing the polymerizable composition is a compound having a norbornene ring. Specific examples include norbornenes, dicyclopentadienes, tetracyclododecenes, and the like. These may have as a substituent a hydrocarbon group such as alkyl group, alkenyl group, alkylidene group, and aryl group; or a polar group such as carboxyl group and acid anhydride residue. Further, in addition to the double bond in the norbornene ring, the norbornene monomer may have a further double bond. Among these, norbornene monomers which do not have a polar group, that is, composed only of carbon atoms and hydrogen atoms are preferred.

Examples of norbornene monomers which do not have a polar group include dicyclopentadienes such as dicyclopentadiene, methyldicyclopentadiene, and dihydrodicyclopentadiene (also known as tricyclo$[5.2.1.0^{2,6}]$dec-8-ene);

tetracyclododecenes such as tetracyclo$[6.2.1.1^{3,6}.0^{2,7}]$dodec-4-ene, 9-methyltetracyclo$[6.2.1.1^{3,6}.0^{2,7}]$dodec-4-ene, 9-ethyltetracyclo$[6.2.1.1^{3,6}.0^{2,7}]$dodec-4-ene, 9-cyclohexyltetracyclo$[6.2.1.1^{3,6}.0^{2,7}]$dodec-4-ene, 9-cyclopentyltetracyclo$[6.2.1.1^{3,6}.0^{2,7}]$dodec-4-ene, 9-methylenetetracyclo$[6.2.1.1^{3,6}.0^{2,7}]$dodec-4-ene, 9-ethylidenetetracyclo$[6.2.1.1^{3,6}.0^{2,7}]$dodec-4-ene, 9-vinyltetracyclo$[6.2.1.1^{3,6}.0^{2,7}]$dodec-4-ene, 9-propenyltetracyclo$[6.2.1.1^{3,6}.0^{2,7}]$dodec-4-ene, 9-cyclohexenyltetracyclo$[6.2.1.1^{3,6}.0^{2,7}]$dodec-4-ene, 9-cyclopentenyltetracyclo$[6.2.1.1^{3,6}.0^{2,7}]$dodec-4-ene, and 9-phenyltetracyclo$[6.2.1.1^{3,6}.0^{2,7}]$dodec-4-ene;

norbornenes such as 2-norbornene, 5-methyl-2-norbornene, 5-ethyl-2-norbornene, 5-butyl-2-norbornene, 5-hexyl-2-norbornene, 5-decyl-2-norbornene, 5-cyclohexyl-2-norbornene, 5-cyclopentyl-2-norbornene, 5-ethylidene-2-norbornene, 5-vinyl-2-norbornene, 5-propenyl-2-norbornene, 5-cyclohexenyl-2-norbornene, 5-cyclopentenyl-2-norbornene, 5-phenyl-2-norbornene, tetracyclo$[9.2.1.0^{2,10}.0^{3,8}]$tetradec-3,5,7,12-tetraene (also known as 1,4-methano-1,4,4a,9a-tetrahydro-9H-fluorene), and tetracyclo$[10.2.1.0^{2,11}.0^{4,9}]$pentadec-4,6,8,13-tetraene (also known as 1,4-methano-1,4,4a,9,9a,10-hexahydroanthracene);

cycloolefins having five or more ring members such as pentacyclo$[6.5.1.1^{3,6}.0^{2,7}.0^{9,13}]$pentadec-4,10-diene, pentacyclo$[9.2.1.1^{4,7}.0^{2,10}.0^{3,8}]$pentadec-5,12-diene, and hexacyclo$[6.6.1.1^{3,6}.1^{10,13}.0^{2,7}.0^{9,14}]$heptadec-4-ene; and the like.

Examples of norbornene monomers which have a polar group include methyl tetracyclo$[6.2.1.1^{3,6}.0^{2,7}]$dodec-9-ene-4-carboxylate, tetracyclo$[6.2.1.1^{3,6}.0^{2,7}]$dodec-9-ene-4-methanol, tetracyclo$[6.2.1.1^{3,6}.0^{2,7}]$dodec-9-ene-4-carboxylic acid, tetracyclo$[6.2.1.1^{3,6}.0^{2,7}]$dodec-9-ene-4,5-dicarboxylic acid, tetracyclo$[6.2.1.1^{3,6}.0^{2,7}]$dodec-9-ene-4,5-dicarboxylic anhydride, methyl 5-norbornene-2-carboxylate, methyl 2-methyl-5-norbornene-2-carboxylate, 5-norbornen-2-yl acetate, 5-norbornen-2-methanol, 5-norbornene-2-ol, 5-norbornene-2-carbonitrile, 2-acetyl-5-norbornene, 7-oxa-2-norbornene and the like.

These norbornene monomers can be used singly or in combination of two or more. It is possible to arbitrarily control the glass transition temperature and melting point of the obtained crosslinkable resin molded article by using two or more monomers and changing their weight ratios.

In addition, the polymerization may be carried out using a monomer mixture prepared by adding a monocyclic cycloolefin, such as cyclobutene, cyclopentene, cyclooctene, cyclododecene, and 1,5-cyclooctadiene or a derivative of the monocyclic cycloolefins having a substituent, to the above-described norbornene monomer. The amount of the monocyclic cycloolefin and derivative thereof is preferably 40% by weight or less, and more preferably 20% by weight or less of the total amount of the norbornene monomer. If the amount of the monocyclic cycloolefin and derivative thereof is more than 40% by weight, the heat resistance of the polymer obtained by bulk polymerization may be insufficient.

(2) Metathesis Polymerization Catalyst

There are no specific limitations on the metathesis polymerization catalyst composing the polymerizable composition, as long as the catalyst can carry out metathesis ring-opening polymerization of the norbornene monomer.

Examples of the metathesis polymerization catalyst include a complex formed from a plurality of ions, atoms, polyatomic ions, and/or compounds bonded to the transition metal atom as the center atom. As the transition metal atom, atoms of groups V, VI, and VIII (in a long periodic-type periodic table, hereinafter the same) may be used. Although there are no specific limitations on the respective atoms belonging to each group, preferred examples include tantalum as the group V atom, molybdenum and tungsten as the group VI atom, and ruthenium and osmium as the group VIII atom.

Of these, it is preferred to use a complex of ruthenium or osmium in the group VIII for the metathesis polymerization catalyst, and a ruthenium-carbene complex is particularly preferred. Since a complex of ruthenium or osmium in the group VIII is so comparatively stable against oxygen or moisture in the atmosphere that the complex is not easily deactivated, the crosslinkable resin can be manufactured even in the atmosphere. Further, a ruthenium carbene complex has excellent catalyst activity in bulk polymerization, and exhibits excellent productivity for a post-crosslinkable resin, thus the crosslinkable resin with substantially no unfavorable odor originating from unreacted monomers can be obtained.

The rutenium-carbene complex is a compound represented by the following formula (1) or (2).

[Chemical Formula 1]

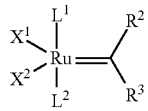
(1)

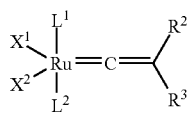
(2)

In the formula (1) and (2), $R^2$ and $R^3$ each independently represent a hydrogen atom, a halogen atom, or a hydrocarbon group having 1 to 20 carbon atoms which may contain halogen atom, oxygen atom, nitrogen atom, sulfur atom, phosphorus atom, or silicon atom. $X^1$ and $X^2$ each independently represent an arbitrary anionic ligand. $L^1$ and $L^2$ each independently represent a hetero atom-containing carbene compound or a neutral electron-donating compound. $R^2$ and $R^3$ may also be bonded to each other to form a ring. The $R^2$, $R^3$, $X^1$, $X^2$, $L^1$, and $L^2$ may also be bonded to each other in an arbitrary combination to form a multidentate chelate ligand.

The hetero atom is an atom of Group XV or XVI in the Periodic Table. Specific examples include N, O, P, S, As, Se and the like. Of these, N, O, P, and S are preferable, and N (nitrogen atom) is particularly preferable, because a stable carbene compound can be obtained.

A hetero atom-containing carbene compound having hetero atoms adjacently bonding to both sides of the carbene carbon atom is preferable, with a carbene compound having a hetero ring which includes a carbene carbon atom and hetero atoms on both sides of the carbene carbon atom being more preferable. It is preferred that the hetero atoms adjacent to the carbene carbon atom have a bulky substituent.

Examples of such a hetero atom-containing carbene compound include compounds represented by the following formula (3) or (4).

[Chemical Formula 2]

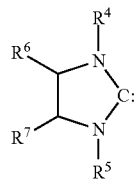
(3)

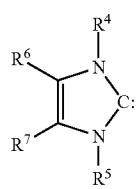
(4)

wherein $R^4$ to $R^7$ each independently represent hydrogen atom, halogen atom, or hydrocarbon group having 1 to 20 carbon atoms which may contain halogen atom, oxygen atom, nitrogen atom, sulfur atom, phosphorus atom, or silicon atom, and $R^4$ to $R^7$ may also be bonded to each other in an arbitrary combination to form a ring.

Examples of compounds represented by the formula (3) or (4) include 1,3-dimesitylimidazolidin-2-ylidene, 1,3-di(1-adamantyl)imidazolidin-2-ylidene, 1-cyclohexyl-3-mesityl-imidazolidin-2-ylidene, 1,3-dimesityloctahydrobenzimidazol-2-ylidene, 1,3-diisopropyl-4-imidazolin-2-ylidene, 1,3-di(1-phenylethyl)-4-imidazolin-2-ylidene, 1,3-dimesityl-2,3-dihydrobenzimidazol-2-ylidene, and the like.

In addition to the compounds represented by the above formula (3) or (4), other hetero atom-containing carbene compounds such as 1,3,4-triphenyl-2,3,4,5-tetrahydro-1H-1,2,4-triazol-5-ylidene, 1,3-dicyclohexylhexahydropyrimidin-2-ylidene, N,N,N',N'-tetraisopropylformamidinylidene, 1,3,4-triphenyl-4,5-dihydro-1H-1,2,4-triazol-5-ylidene, and 3-(2,6-diisopropylphenyl)-2,3-dihydrothiazol-2-ylidene can be used.

In the above formulas (1) and (2), the anionic (negative ionic) ligands $X^1$ and $X^2$ is a ligand having a negative charge when separated from the central metal atom. Examples of these ligands include halogen atoms such as fluorine atom, chlorine atom, bromine atom, and iodine atom; diketonate group, substituted cyclopentadienyl group, alkoxy group, aryloxy group, carboxyl group and the like. Of these, halogen atoms are preferable, and chlorine atom is more preferable.

The neutral electron-donating compound may be any ligand having a neutral charge when separated from the central metal. Specific examples thereof include carbonyls, amines, pyridines, ethers, nitriles, esters, phosphines, thioethers, aromatic compounds, olefins, isocyanides, thiocyanates and the like. Of these, phosphines, ethers, and pyridines are preferable, and trialkylphosphine is more preferable.

Examples of the complex compound represented by the above formula (1) include ruthenium complex compounds in which one of an $L^1$ and $L^2$ is a hetero atom-containing carbene compound and the other is a neutral electron-donating compound, such as benzylidene(1,3-dimesitylimidazolidin-2-ylidene)(tricyclohexylphosphine)ruthenium dichloride, benzylidene(1,3-dimesityl-4,5-dibromo-4-imidazolin-2-ylidene)(tricyclohexylphosphine)ruthenium dichloride, (1,3-dimesityl-4-imidazolin-2-ylidene)(3-phenyl-1H-inden-1-ylidene)(tricyclohexylphosphine)ruthenium dichloride, (1,3-dimesitylimidazolidin-2-ylidene)(3-methyl-2-butene-1-ylidene)(tricyclopentylphosphine)ruthenium dichloride, benzylidene(1,3-dimesityl-octahydrobenzimidazol-2- ylidene)(tricyclohexylphosphine)ruthenium dichloride, benzylidene[1,3-di(1-phenylethyl)-4-imidazolin-2-ylidene](tricyclohexylphosphine)ruthenium dichloride, benzylidene(1,3-dimesityl-2,3-dihydrobenzimidazol-2-ylidene)(tricyclohexylphosphine)ruthenium dichloride, benzylidene(tricyclohexylphosphine)(1,3,4-triphenyl-2,3,4,5-tetrahydro-1H-1,2,4-triazol-5-ylidene)ruthenium dichloride, (1,3-diisopropylhexahydropyrimidin-2-ylidene)(ethoxymethylene)(tricyclohexylphosphine)ruthenium dichloride, benzylidene(1,3-dimesitylimidazolidin-2-ylidene)pyridineruthenium dichloride, (1,3-dimesitylimidazolidin-2-ylidene) (2-phenylethylidene)(tricyclohexylphosphine)ruthenium dichloride, (1,3-dimesityl-4-imidazolin-2-ylidene)(2-phenylethylidene)(tricyclohexylphosphine)ruthenium dichloride, (1,3-dimesityl-4,5-dibromo-4-imidazolin-2-ylidene)[(phenylthio)methylene](tricyclohexylphosphine)ruthenium dichloride, and (1,3-dimesityl-4,5-dibromo-4-imidazolin-2-ylidene) (2-pyrolidon-1-ylmethylene)(tricyclohexylphosphine)ruthenium dichloride;

ruthenium complex compounds in which both $L^1$ and $L^2$ are neutral electron-donating compounds, such as benzylidenebis(tricyclohexylphosphine)ruthenium dichloride, and (3-methyl-2-buten-1-ylidene) bis(tricyclopentylphosphine)ruthenium dichloride; and ruthenium complex compounds in which both $L^1$ and $L^2$ are hetero atom-containing carbene compounds, such as benzylidenebis(1,3-dicyclohexylimidazolidin-2-ylidene)ruthenium dichloride, and benzylidenebis(1,3-diisopropyl-4-imidazolin-2-ylidene)ruthenium dichloride; and the like.

Examples of the complex compound in which $R^2$ and $L^1$ are bonded in the above formula (1) include the compounds represented by the following formulas (5) to (7). iPr represents an isopropyl group.

[Chemical Formula 3]

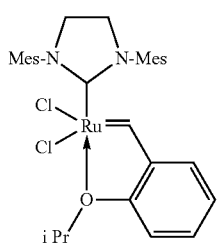

(5)

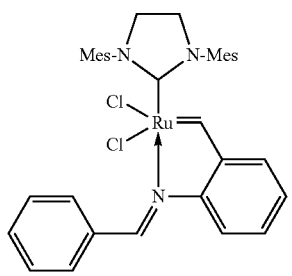

(6)

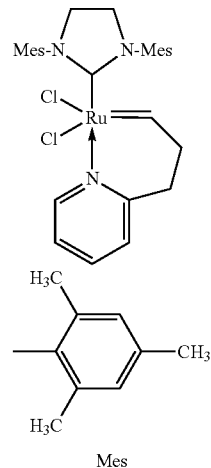

(7)

Examples of complex compounds represented by the above formula (2) include (1,3-dimesitylimidazolidin-2-ylidene) (phenylvinylidene)(tricyclohexylphosphine)ruthenium dichloride, (t-butylvinylidene)(1,3-diisopropyl-4-imidazolin-2-ylidene)(tricyclopentylphosphine)ruthenium dichloride, bis(1,3-dicyclohexyl-4-imidazolin-2-ylidene) phenylvinylideneruthenium dichloride and the like.

Of these complex compounds, ruthenium complex compounds which are represented by the above formula (1), and in which one of $L^1$ and $L^2$ is a compound represented by the above formula (4) and the other is a neutral electron-donating compound, are most preferred.

These metathesis polymerization catalysts can be manufactured by the methods described in Org. Lett., 1999, Vol. 1, p. 953 and Tetrahedron. Lett., 1999, Vol. 40, p. 2247, for example.

The metathesis polymerization catalyst is used in a molar ratio (the metal atom in the catalyst to the norbornene monomer) usually in the range of 1:2,000 to 1:2,000,000, preferably 1:5,000 to 1:1,000,000, and more preferably 1:10,000 to 1:500,000.

The metathesis polymerization catalyst may be used optionally by dissolving or suspending the catalyst in a small amount of an inert solvent. Examples of the solvent include chain aliphatic hydrocarbons such as n-pentane, n-hexane, n-heptane, liquid paraffin, and mineral spirit; alicyclic hydrocarbons such as cyclopentane, cyclohexane, methylcyclohexane, dimethylcyclohexane, trimethylcyclohexane, ethylcyclohexane, diethylcyclohexane, decahydronaphthalene, dicycloheptane, tricyclodecane, hexahydroindene, and cyclooctane; aromatic hydrocarbons such as benzene, toluene, and xylene; hydrocarbons having a condensed ring of an aromatic ring and an alicyclic ring such as indene, indane, and tetrahydronaphthalene; nitrogen-containing hydrocarbons such as nitromethane, nitrobenzene, and acetonitrile; and oxygen-containing hydrocarbons such as diethyl ether and tetrahydrofuran. Of these, it is preferred to use industrial general purpose hydrocarbons. In addition, a liquid antiaging agent, liquid plasticizer, or liquid elastomer may also be used as the solvent as long as the activity of the metathesis polymerization catalyst is not reduced.

An activator (co-catalyst) may be used in combination with the metathesis polymerization catalyst to control the polymerization activity or to improve the rate of the polymerization reaction. Examples of the activator include alkyl compounds, halides, alkoxy compounds, and aryloxy compounds, of aluminum, scandium, or tin, and the like.

Specific examples of the activator include trialkoxy aluminum, triphenoxy aluminum, dialkoxyalkyl aluminum, alkoxydialkyl aluminum, trialkyl aluminum, dialkoxy aluminum chloride, alkoxyalkyl aluminum chloride, dialkyl aluminum chloride, trialkoxy scandium, tetraalkoxy titanium, tetraalkoxy tin, tetraalkoxy zirconium and the like.

The activator is used in a molar ratio (the metal atom in the metathesis polymerization catalyst to the activator) usually in the range of 1:0.05 to 1:100, preferably 1:0.2 to 1:20, and more preferably 1:0.5 to 1:10.

When the complex of a transition metal atom in Group V and Group VI is used as a metathesis polymerization catalyst, it is preferred that both the metathesis polymerization catalyst and the activator are dissolved in the monomer. However, it is possible to dissolve or suspend the metathesis polymerization catalyst and the activator in a small amount of solvent as long as the properties of the resulting product are not essentially impaired.

(3) Chain Transfer Agent

The chain transfer agent used in the polymerizable composition of the present invention is composed of a compound represented by formula (A):

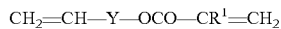

$$CH_2=CH-Y-OCO-CR^1=CH_2$$

wherein Y represents a divalent hydrocarbon group having 3 to 20 carbon atoms, and $R^1$ represents a hydrogen atom or a methyl group.

Examples of the divalent hydrocarbon group Y include alkylene group, phenylene group and so on. From the standpoint of excellent metathesis reactivity, Y is preferably alkylene group. The alkylene group preferably has 4 to 15 carbon atoms, more preferably 4 to 12 carbon atoms, still more preferably 4 to 11 carbon atoms, and especially preferably 5 to 8 carbon atoms.

Specific examples of the compound represented by the formula (A) include undecenyl methacrylate, decenyl methacrylate, nonenyl methacrylate, octenyl methacrylate, heptenyl methacrylate, hexenyl methacrylate, pentenyl methacrylate, undecenyl acrylate, decenyl acrylate, nonenyl acrylate, octenyl acrylate, heptenyl acrylate, hexenyl acrylate, pentenyl acrylate and the like. Of these, preferred are nonenyl methacrylate, octenyl methacrylate, heptenyl methacrylate, hexenyl methacrylate, and pentenyl methacrylate.

Since these chain transfer agents have high metathesis reactivity, it is easy to obtain a crosslinkable resin with a narrow molecular weight distribution. Therefore, when the crosslinkable resin in heated on the support, the fluidity of the resin tends to be uniform, so that the embeddability of the resin into the support surface improves.

The added amount of the chain transfer agent is usually in the range of 0.01 to 10% by weight, and preferably 0.1 to 5% by weight, based on the total amount of the norbornene monomer. If the added amount of the chain transfer agent is in this range, the polymerization reaction rate is high, and a post-crosslinkable thermoplastic resin can be efficiently obtained.

Further, since the residual amount of the chain transfer agent after the polymerization is small, a resin having a small dielectric loss (tan δ) can be obtained.

(4) Crosslinking Agent

To obtain a resin having crosslinkability even after the bulk polymerization, the polymerizable composition preferably comprises a crosslinking agent.

Examples of the crosslinking agent include radical generating agents, epoxy compounds, isocyanate group containing compounds, carboxyl group containing compounds, acid anhydride residue containing compounds, amino group containing compounds, Lewis acids and the like. These crosslinking agents can be used either individually or in combination of two or more. Among them, it is preferred to use radical generating agents, epoxy compounds, isocyanate group containing compounds, carboxyl group containing compounds, or acid anhydride residue containing compounds. More preferred is to use radical generating agents, epoxy compounds, or isocyanate group containing compounds, and especially preferred is to use radical generating agents.

Examples of the radical generating agent include organic peroxides, diazo compounds, and nonpolar radical generating agents. Examples of the organic peroxide include hydroperoxides such as t-butyl hydroperoxide, p-menthane hydroperoxide, and cumene hydroperoxide; dialkyl peroxides such as dicumyl peroxide, t-butyl cumyl peroxide, α,α'-bis(t-butylperoxy-m-isopropyl)benzene, di-t-butyl peroxide, 2,5-dimethyl-2,5-di(t-butylperoxy)-3-hexine, and 2,5-dimethyl-2,5-di(t-butylperoxy)hexane; diacyl peroxides such as dipropionyl peroxide and benzoyl peroxide; peroxyketals such as 2,2-di(t-butylperoxy)butane, 1,1-di(t-hexylperoxy)cyclohexane, 1,1-di(t-butylperoxy)-2-methylcyclohexane, and 1,1-di(t-butylperoxy)cyclohexane; peroxy esters such as t-butylperoxy acetate and t-butylperoxy benzoate; peroxycarbonates such as t-butylperoxy isopropylcarbonate and di(isopropylperoxy) dicarbonate; alkylsilylperoxides such as t-butyltrimethylsilyl peroxide, and the like. Of these, dialkyl peroxides and peroxyketals are preferable due to a small hindrance on the metathesis polymerization reaction.

Examples of the diazo compound include 4,4'-bisazidobenzal(4-methyl)cyclohexanone, 4,4'-diazidochalcone, 2,6-bis(4'-azidobenzal)cyclohexanone, 2,6-bis(4'-azidobenzal)-4-methylcyclohexanone, 4,4'-diazidodiphenylsulfone, 4,4'-diazidodiphenylmethane, 2,2'-diazidostilbene, and the like.

Examples of the nonpolar radical generating agent include 2,3-dimethyl-2,3-diphenylbutane, 2,3-diphenylbutane, 1,4-diphenylbutane, 3,4-dimethyl-3,4-diphenylhexane, 1,1,2,2-tetraphenylethane, 2,2,3,3-tetraphenylbutane, 3,3,4,4-tetraphenylhexane, 1,1,2-triphenylpropane, 1,1,2-triphenylethane, triphenylmethane, 1,1,1-triphenylethane, 4,5-dimethyl-4,5-diphenyloctane, 1,1,1-triphenylpropane, 1,1,1-triphenylbutane, 1,1,1-triphenylpentane, 1,1,1-triphenyl-2-propene, 1,1,1-triphenyl-4-pentene, 1,1,1-triphenyl-2-phenylethane and the like.

These radical generating agents may be used as single or in combination of two or more. It is possible to arbitrarily control the glass transition temperature and melting condition of the obtained crosslinkable resin by using two or more of these radical generating agents and varying their weight ratios. The radical generating agent used in the present invention has a one minute half-life temperature of preferably 150° C. to 350° C., and more preferably of 200° C. to 300° C. In the present invention, the "one minute half-life temperature" represents the temperature at which half of the radical generating agent decomposes in one minute. Among radical generating agents, a nonpolar radical generating agent is preferred. The nonpolar radical generating agent is a compound having a dipole moment of 0.5 or less which can generate a radical by heating, and which can initiate a crosslinking reaction. The dipole moment is preferably 0.3 or less, and more preferably 0.15 or less.

The used amount of the crosslinking agent is usually 0.1 to 10 parts by weight, and preferably 0.5 to 5 parts by weight, based on 100 parts by weight of the norbornene monomer. If the amount of the crosslinking agent is too low, the crosslinking is insufficient, which can make it difficult to obtain a crosslinked resin with a high crosslinking density. If the amount of the crosslinking agent is too high, even though the crosslinking effects become saturated, it can be difficult to obtain a thermoplastic resin and a crosslinked resin having the desired physical properties.

In the present invention, when a radical generating agent is used as the crosslinking agent, a crosslinking aid may be used to accelerate the crosslinking reaction. Examples of the crosslinking aid include dioxime compounds such as p-quinone dioxime; methacrylate compounds such as lauryl methacrylate and trimethylolpropane trimethacrylate; fumaric acid compounds such as a diallyl fumarate; phthalic acid compounds such as a diallyl phthalate; cyanuric acid compounds such as triallyl cyanurate and trimethallyl cyanurate; imide compounds such as maleimide and the like. Further, compounds having two or more isopropenyl groups, such as diisopropenylbenzene, triisopropenylbenzene, and trimethallyl isocyanate, may also be preferably used. Although there are no specific limitations, the used amount of the crosslinking aid is usually 0 to 100 parts by weight, and preferably 0 to 50 parts by weight, based on 100 parts by weight of the norbornene monomer.

(5) Other Additives

Various additives, for example, a polymerization reacting retarder, a radical crosslinking retarder, a reinforcing material, a modifier, an antioxidant, a flame retardant, a filler, a coloring agent, and a light stabilizer can be added to the polymerizable composition. These additives may be dissolved or dispersed in the below-described monomer liquid or catalyst liquid beforehand.

Examples of the polymerization reacting retarder include phosphines such as triphenylphosphine, tributylphosphine, trimethylphosphine, triethylphosphine, dicyclohexylphosphine and vinyl diphenylphosphine; and Lewis bases such as aniline and pyridine. Of these, phosphines are preferred, as they can efficiently control the pot life of the polymerizable composition, and do not interfere much in the polymerization reaction.

Of the cycloolefin monomers which are capable of copolymerization with the norbornene monomer, cycloolefins having 1,5-diene structure or 1,3,5-triene structure in the molecule also function as a polymerization reacting retarder. Examples of such compounds include 1,5-cyclooctadiene and 5-vinyl-2-norbornene.

Examples of the radical crosslinking retarder include alkoxyphenols, catechols, and benzoquinones, and alkoxyphenols such as 3,5-di-t-butyl-4-hydroxyanisol is preferred.

Examples of the reinforcing material include short fiber powders such as chopped strands, milled fibers and the like. Examples of the kinds of such fibers include glass fiber, paper substrate, carbon fiber, metal fiber, aramid fiber and the like. Examples of the modifier include elastomers such as natural rubber, polybutadiene, polyisoprene, styrene-butadiene copolymer (SBR), styrene-butadiene-styrene block copolymer (SBS), styrene-isoprene-styrene block copolymer (SIS), ethylene-propylene-diene terpolymer (EPDM), ethylene-vinyl acetate copolymer (EVA), and their hydrogenated products; and the like. Examples of the antioxidant include various antioxidants for plastic or rubber such as hindered phenol antioxidants, phosphorus antioxidants, amine antioxidants and the like. These antioxidants can be used singly, or preferably in combination of two or more.

Examples of the flame retardant include phosphorus-containing flame retardants, nitrogen-containing flame retardants, halogen-containing flame retardants, metal hydroxide flame retardants such as aluminum hydroxide, antimony compounds such as antimonous oxide, and the like. These flame retardants can be used singly, or preferably in combination of two or more.

Examples of the filler include glass powder, ceramic powder, silica and the like. These fillers may be used in combination of two or more. The filler may also be subjected to a surface treatment by a silane coupling agent and the like. The amount of the filler is usually 0 to 600 parts by weight, preferably 50 to 500 parts by weight, and more preferably 50 to 300 parts by weight, based on 100 parts by weight of the norbornene monomer.

As the coloring agent, a dye or a pigment may be used. There are many kinds of dyes, and a well-known kind may be appropriately selected and used.

The polymerizable composition is not especially limited by the manufacturing method thereof. For example, the polymerizable composition may be produced by preparing a liquid matter (hereinafter, sometimes referred to as "catalyst liquid") in which the metathesis polymerization catalyst was dissolved or dispersed in an appropriate solvent, and preparing an added liquid matter (hereinafter, sometimes referred to as "monomer liquid") in which the norbornene monomer is blended as necessary with additives such as a filler and a flame retardant, then mixing the catalyst liquid into the monomer liquid and stirring the resulting mixture. The mixing of the monomer liquid and the catalyst liquid is preferably carried out immediately before the following-described bulk polymerization. Further, the chain transfer agent, crosslinking agent, radical crosslinking retarder and the like may be added to the monomer liquid and/or catalyst liquid before mixing the monomer liquid and the catalyst liquid, or to the mixture of the monomer liquid and the catalyst liquid.

[Crosslinkable Resin and Crosslinkable Resin Composite]

The crosslinkable resin in the present invention may be obtained by carrying out bulk polymerization of the above-described polymerizable composition.

Examples of the method for carrying out bulk polymerization of the polymerizable composition include: (a) a method comprising the steps of pouring or coating the polymerizable composition onto a support and then carrying out the bulk polymerization of the polymerizable composition; (b) a method comprising the steps of pouring the polymerizable composition into a mold, and then carrying out the bulk polymerization of the polymerizable composition; and (c) a method comprising the steps of impregnating the polymerizable composition into a support, and then carrying out the bulk polymerization of the polymerizable composition and the like. If the polymerizable composition is subjected to bulk polymerization according to the method (a) or (c), a crosslinkable resin composite which comprises the support and the crosslinkable resin is obtained.

A crosslinkable resin composite composed of the crosslinkable resin and the support can be obtained if the method (a) is followed. Examples of the support used here include resins such as polyethylene terephthalate, polypropylene, polyethylene, polycarbonate, polyethylene naphthalate, polyarylate, and nylon; metal materials such as iron, stainless steel, copper, aluminum, nickel, chromium, gold, silver and the like. Although there are no specific limitations as to the shape of the support, a metal foil or a resin film is preferably used. For example, if a copper foil is used for the support, resin coated copper (RCC) foil can be obtained. The thickness of the metal foil or resin film is usually 1 to 150 μm, preferably 2 to 100 μm, and more preferably 3 to 75 μm from the standpoint of workability and the like. The surface of the support is preferably smooth. Further, the support surface has preferably been subjected to surface treatment with a silane coupling agent such as styryltrimethoxysilane and the like.

There are no specific limitations on the method of coating the polymerizable composition onto the support. Examples thereof include well-known methods such as a spray coating method, a dip coating method, a roll coating method, a curtain coating method, a die coating method, a slit coating method and the like.

The bulk polymerization is started by heating the polymerizable composition to a temperature at which the metathesis polymerization proceeds.

The method of heating the polymerizable composition to a prescribed temperature is not especially limited. Examples include a method of heating by placing on a heating plate, a method of heating (hot-pressing) while applying pressure using a press machine, a method of pressing using a heated roller, a method of using a furnace and the like.

The thickness of the crosslinkable resin film obtained in the above manner is usually 15 mm or less, preferably 10 mm or less, more preferably 5 mm or less, and especially preferably 1 mm or less.

A crosslinkable resin molded article in an arbitrary shape can be obtained if the method (b) is followed. Examples of the shape of the molded article include a sheet, film, column, cylinder, polygonal column and the like.

As the mold used here, a commonly known mold, for example, a split mold having a core die and a cavity die can be used, by injecting the polymerizable composition into the void part (mold cavity) and carrying out the bulk polymerization therein. The core and cavity dies are fabricated so that a void part may be provided conforming to the shape of a desired molded product. There are no specific limitations on the shape, material, or size of the mold. A molded article of the crosslinkable resin in the form of a sheet or a film can also be obtained by providing plate-like dies such as a glass plate or a metal plate and a spacer with a prescribed thickness which is interposed between two of the plate-like dies, and injecting the polymerizable composition into the space formed by two of the plate-like dies and the spacer.

The filling pressure (injection pressure) for filling the polymerizable composition into the cavity of the mold is usually 0.01 to 10 MPa, and preferably 0.02 to 5 MPa. If the filling pressure is too low, there is a tendency for the transfer surface formed in the inner surface of the cavity not to be transferred in a proper manner. Too high filling pressure requires a highly rigid mold and is, therefore, uneconomical. The mold clamping pressure is usually within the range of 0.01 to 10 MPa.

The support which is used in the method (c) is a fiber material. According to this method, a prepreg, which is a crosslinkable resin composite, in which the crosslinkable resin is impregnated in the fiber material can be obtained. The fiber material used here may be an organic and/or inorganic fiber. Examples thereof include known fibers such as glass fiber, carbon fiber, aramid fiber, polyethylene terephthalate fiber, vinylon fiber, polyester fiber, amide fiber, metal fiber, and ceramic fiber. These fibers can be used singly or in combination of two or more. Examples of the form of the fiber material include a mat, cloth, nonwoven fabric and the like. Further, the surface of the fiber material has preferably been subjected to surface treatment with a silane coupling agent and the like.

The impregnation of the polymerizable composition into the fiber material may be carried out, for example, by a method comprising the steps of coating the prescribed amount of the polymerizable composition onto the fiber material by a known method such as spray coating, dip coating, roll coating, curtain coating, die coating, or slit coating, layering a protective film over the coated polymerizable composition, as required, and pressing the resulting material using a roller or the like. After the fiber material has been impregnated with the polymerizable composition, the resulting impregnated product is heated to the prescribed temperature to carry out bulk polymerization of the polymerizable composition, whereby a crosslinkable resin-impregnated prepreg can be obtained.

There are no specific limitations on the method of heating the impregnated product. For example, the above-mentioned method (a) can be employed, or in which the impregnated product may be placed on a substrate and heated. Alternatively, the polymerizable composition may be injected into a mold in which the fiber material has been set to impregnate the polymerizable composition into the fiber material, and then the bulk polymerization may be carried out by following the method (b).

Since the polymerizable composition has a lower viscosity than conventional resin varnishes, and has excellent impregnation properties with respect to the fiber material, the crosslinkable resin can be uniformly impregnated into the fiber material.

Because the polymerizable composition contains only a small amount of the solvent and the like which do not participate in the reaction, a step of removing the solvent after impregnation into the fiber material or the like is not required. Thus, productivity is good and problems due to the remaining solvent such as odor, blister and the like do not occur. Furthermore, since the crosslinkable resin in the present invention has excellent storage stability, the obtained prepreg also has excellent storage stability.

In any of the above methods (a), (b), and (c), the heating temperature for polymerizing the polymerizable composition is usually 50 to 250° C., and preferably 100 to 200° C. The polymerization time may be appropriately selected, and is usually 10 seconds to 20 minutes, and preferably within 5 minutes.

The polymerization reaction starts when the polymerizable composition is heated to a predetermined temperature. This polymerization reaction is an exothermic reaction. Thus, once the bulk polymerization starts, the temperature of the reaction solution will rapidly increase and reach a peak temperature in a short time (e.g., about 10 seconds to 5 minutes). If the maximum temperature during the polymerization reaction is too high, the crosslinking reaction may also proceed, whereby a crosslinked body is obtained. This can make it difficult to obtain the post-crosslinkable resin. Therefore, to ensure that only the polymerization reaction completely proceeds and to inhibit the crosslinking reaction, it is preferred to control the peak temperature of bulk polymerization to usually not more than the one minute half-life temperature of the radical generating agent, preferably to not more than 230° C., and more preferably to less than 200° C.

The crosslinkable resin in the present invention is post-crosslinkable. The term "post-crosslinkable" herein refers to the ability for the resin to become a crosslinked body when the resin is heated due to a crosslinking reaction proceeding.

Further, the crosslinkable resin composite in the present invention is a complex material in which the above-described crosslinkable resin and the above-described support are integrally formed.

Since the bulk polymerization of the polymerizable composition almost completely proceeds, the crosslinkable resin of the present invention contains only a small amount of residual chain transfer agent. Thus, the dielectric loss (tan δ) of the obtained crosslinked body is greatly reduced, so that the electric properties are excellent. This amount is, based on the added amount, preferably 5% or less, more preferably 3% or less, and most preferably 1.5% or less. The amount of residual chain transfer agent can be determined by dissolving the crosslinkable resin in a solvent and analyzing the resulting solution using gas chromatography, for example.

Further, according to the present invention, a crosslinkable resin with a narrow molecular weight distribution can be obtained. As a result, since the molecular weight is uniform, the fluidity of the resin tends to be uniform, so that the embeddability into the support surface improves. This molecular weight distribution is, in terms of the ratio (Mw/Mn) of weight average molecular weight (Mw) to number average molecular weight (Mn), preferably 3 or less, more preferably 2.3 or less, and most preferably 2 or less. Further, the range of the weight average molecular weight is preferably 5,000 to 80,000, more preferably 10,000 to 50,000, and most preferably 15,000 to 30,000. If the molecular weight is too low, fluidity becomes too high, so that it may become difficult to control the embeddability of the resin into the support and the flatness. Further, if the molecular weight is too high, the resin may not flow at the temperature range of during the crosslinking.

The crosslinkable resin in the present invention preferably is soluble in a solvent including aromatic hydrocarbons such as benzene and toluene, ethers such as diethyl ether and tetrahydrofuran, and halogenated hydrocarbons such as dichloromethane and chloroform, and the like. Further, since the crosslinkable resin in the present invention exhibits thermoplastic properties, the crosslinkable resin can be formed into various shapes by melt molding at a temperature where the crosslinking reaction does not occur.

The molded article of the crosslinkable resin in the present invention may be a partially crosslinked body. For example, when the polymerizable composition is subjected to bulk polymerization in the mold, it is difficult for the heat generated by the polymerization reaction to radiate at the center of the mold. As a result, the temperature on a part in the mold can become too high. The crosslinking reaction proceeds in the high-temperature portion, thereby manufacturing a crosslinked body in this portion. However, if the surface portions which tend to radiate heat are formed from a post-crosslinkable resin, the effects as a molded article of the crosslinkable resin in the present invention can be sufficiently enjoyed. Even for the composite of the crosslinkable resin, part of the crosslinkable resin may be a crosslinked body in a similar way.

Since the crosslinkable resin in the present invention is obtained as a result of almost complete progress of the bulk polymerization, there is no risk of further progress of the polymerization reaction during storage. Although the crosslinkable resin in the present invention contains a crosslinking agent (nonpolar radical generating agent), unless the resin is heated to at least a temperature where the crosslinking reaction would proceed, problems such as changes in the surface hardness do not arise. The present crosslinkable resin thus has excellent storage stability.

[Crosslinked Body]

The crosslinked body in the present invention is formed by crosslinking the above-described crosslinkable resin.

The crosslinking of the crosslinkable resin can be carried out by maintaining the resin at not less than a temperature where the crosslinking reaction of the resin proceeds, for example, by heating and melting the resin of the present invention. The temperature necessary for crosslinking of the crosslinkable resin is preferably higher than the peak temperature during the bulk polymerization by not less than 20° C. Usually, this temperature is 170 to 250° C., and more preferably 180 to 220° C. Although there are no specific limitations, the crosslinking time is usually from several minutes to several hours.

When the crosslinkable resin is a molded article in the form of a sheet or a film, the molded article is preferably laminated on a substrate and heat-pressed as necessary. The pressure applied for press-heating is usually 0.5 to 20 MPa, and preferably 3 to 10 MPa. The heat-pressing may be carried out in a vacuum or under a reduced pressure atmosphere. The heat-pressing may be carried out using a known pressing machine having a press frame mold for forming plates, a press-forming machine such as an SMC (sheet mold compound) or a BMC (bulk mold compound) and the like.

[Crosslinked Resin Composite]

The crosslinked resin composite in the present invention comprises the above-described crosslinked body and the support.

The crosslinked resin composite in the present invention is obtained by crosslinking the above-described crosslinkable resin composite. The crosslinked resin composite may be obtained by heating and crosslinking the crosslinkable resin molded article on a support, or by heating and crosslinking the crosslinkable resin composite on another support.

Examples of the method of heating and crosslinking the crosslinkable resin molded article or crosslinkable resin composite on a support include hot-pressing. For example, a crosslinkable resin in the form of a plate or a film may be laminated with a support, and further heated to crosslink the crosslinkable resin by heat-pressing. The heat-press conditions may be the same as those for the crosslinking of the above crosslinkable resin.

Examples of new support which may be used here include metal foils such as copper foil, aluminum foil, nickel foil, chromium foil, gold foil, and silver foil; a printed circuit board; films such as a conductive polymer film and other resin films; and the like. If a printed circuit board is used as the support, a multilayer printed circuit board can be manufactured.

It is preferred to treat a surface of the metal foil, such as copper foil, or the conductive layer on the printed circuit board with a silane coupling agent, a thiol coupling agent, a titanate coupling agent, or various types of adhesive. Of these, it is especially preferred to treat the surface with a silane coupling agent.

Since the crosslinkable resin in the present invention is excellent in fluidity and adhesion, a composite being excellent in smoothness and adhesion with the support can be obtained. For example, even when a super low profile (SLP) copper foil is used as the support, the composite in the present invention preferably has a peel strength as measured based on JIS C6481 of 0.4 kN/m or more, and more preferably 0.6 kN/m or more.

The crosslinked body and composite in the present invention are excellent in electric insulation, mechanical strength, heat resistance, dielectric properties and the like. Further, the composite has excellent adhesion with the support, and is suitable as an electric material.

EXAMPLES

The present invention will now be described in detail by way of examples and comparative examples, which should not be construed as limiting the present invention. In the examples and comparative examples below "parts" and "%" are indicated on a weight basis, unless otherwise specified.

In the present examples, evaluation was carried out based on the following methods.

(Number Average Molecular Weight (Mn), Weight Average Molecular Weight (Mw), and Molecular Weight Distribution (Mw/Mn))

These were determined by converting the measurement results from gel permeation chromatography using tetrahydrofuran as a developing solution into a molecular weight of standard polystyrene.

(Residual Ratio of the Chain Transfer Agent)

A prepreg cut into 30 mm square was put into a glass bottle. Toluene was poured into the bottle to dissolve the polymer portion of the prepreg. The resultant solution was charged into a separately-prepared glass bottle containing isopropyl alcohol. Finally, the supernatant was sucked into a plastic syringe provided with a filter, and measurement was carried out by gas chromatography. The amount of residual chain transfer agent was determined from a pre-measured calibration curve of the chain transfer agent, and taken as residual chain transfer agent/added chain transfer agent×100(%).

D: More than 5.0%

C: More than 3.0% and not more than 5.0%

B: More than 1.5% and not more than 3.0%

A: not more than 1.5%

(Lamination Properties)

The lamination properties were determined by visually observing a crosslinked resin composite B and evaluating according to the following standards.

D: Bumps on the copper foil surface, and thin spots observed on the whole front face and cross-section surface after the copper foil peeling.

C: Any one of bumps on the copper foil surface or thin spots observed on the front face and cross-section surface after the copper foil peeling.

B: Less than 5% by aera of bumps over the entire copper foil surface or less than 5% by area of thin spots observed on the front face and cross-section surface after the copper foil peeling.

A: No bumps and no thin spots. Flat.

Here, "bumps" refer to the condition where bumps are formed along the traces of the wiring following an IPC standard wiring pattern, or where such bumps are visually observed. Further, "thin spots" refers to the condition where a space is manufactured between different materials, such as the copper foil and the resin, the resin and the glass cloth, the resin and the IPC substrate. For products without any bumps, the laminate will be flat irrespective of whether a wiring pattern is present or not.

(Peel Strength)

The peel strength was measured as the strength when a 12 μm SLP copper foil which is laminated on a crosslinked resin composite A was peeled based on JIS C6481. The peel strength was evaluated according to the following index based on that measured value.

D: More than 0.1 kN/m and not more than 0.4 kN/m

C: More than 0.4 kN/m and not more than 0.6 kN/m

B: More than 0.6 kN/m and not more than 0.7 kN/m

A: More than 0.7 kN/m (Dielectric Loss (tan δ))

The dielectric loss (tan δ) at a 1 GHz frequency was measured by a capacitance method using an impedance analyzer (manufactured by Agilent Technologies, Model No. E4991). The dielectric loss was evaluated according to the following index based on that measured value.

C: More than 0.0020

B: More than 0.0015 and not more than 0.0020

A: not more than 0.0015

Example 1

In a flask made of glass, 0.04 part of benzylidene(1,3-dimethyl-4-imidazolin-2-ylidene) (tricyclohexylphosphine) ruthenium dichloride and 0.06 part of triphenylphosphine were dissolved in 0.7 part of tetrahydrofuran to prepare a catalyst liquid.

Into a 200 mL metal container, 70 parts of tetracyclo[6.2.1.1$^{3,6}$.0$^{2,7}$]dodec-4-ene, 30 parts of 2-norbornene, 100 parts of silica particles, 10 parts of an antimony oxide as a flame retardant (PATOX-M, manufactured by Nihon Seiko Co., Ltd.) and 26.7 parts of ethan-1,2-bis(pentabromophenyl) (SAYTEX 8010, manufactured by Albemarle Corporation) were charged. The resultant material was uniformly mixed to obtain a monomer liquid.

Next, into a bottle (outer diameter 50 mm) made of polyethylene with a volume of 200 mL, 240 parts of the above monomer liquid, 1.8 parts of hexenyl methacrylate (Economer ML, C5 type, manufactured by Shin Nakamura Chemical Corporation) as a chain transfer agent, 1 part of a tertiary butyl-peroxide (one minute half-life temperature of 186° C., Perbutyl D, manufactured by NOF Corporation) as a crosslinking agent, and 0.35 part of the above catalyst liquid were charged under stirring to obtain a polymerizable composition.

Next, 70 parts of this polymerizable composition was flow-cast on a polyethylene naphthalate film (Type Q51, thickness of 75 μm, manufactured by DuPont Teijin Films Japan Limited). Then, a glass cloth (2116-silane coupling agent treated product, thickness of 75 μm) was laid over this, and 70 parts of the above polymerizable composition was further flow-cast over the glass cloth. A polyethylene naphthalate film was then covered over the top of this, and the polymerizable composition was impregnated into the whole of the glass cloth using a roller. Then, the resultant product was heated for 1 minute in a heating furnace heated to 130° C. to bulk-polymerize the polymerizable composition, whereby a crosslinkable resin composite as a prepreg was obtained. The molecular weight of the bulk polymer moiety in this prepreg was measured to be as follows: Mn=11,600; Mw=22,000; and Mw/Mn=1.9.

This prepreg was cut into a size having 100 mm square, and 6 sheets thereof were stacked upon each other. Both sides of the resultant laminate were sandwiched with SLP copper foils (Type F0, thickness of 0.0012 mm, silane coupling agent surface treated product, manufactured by Furukawa Circuit Foil Co., Ltd.), and then heat-pressed for 30 minutes at 200° C. under 3 MPa by a hot press to produce a crosslinked resin composite A.

The obtained crosslinked resin composite A was cut into a 25 mm×100 mm size. The peel strength was measured to be 0.7 kN/m.

This crosslinked resin composite A was cut into a 20 mm×20 mm size, and this sheet was dipped in ferric chloride solution (manufactured by Sunhayato Corp.) at 40° C. to remove the copper foil from the surface. The dielectric loss (tan δ) of the crosslinked resin composite A from which the copper foil had been removed was 0.0015.

By the same procedures, one prepreg sheet with 100 mm square was placed on an IPC substrate (IPC standard multi-purpose substrate). A copper foil was placed on the prepreg sheet, and the resultant laminate was heat-pressed for 30 minutes at 200° C. under 3 MPa by a hot press to produce a crosslinked resin composite B.

When both the surface and a cross section of the crosslinked resin composite B were observed for copper foil surface bumpiness and thinning phenomenon after copper foil peeling, no bump nor thin spot was found.

From the above results, it can be seen that by hot pressing a prepreg obtained by subjecting the polymerizable composition in the present invention to bulk polymerization, the crosslinkable resin in the fiber material formed by the bulk polymerization of the polymerizable composition fuses and adheres to the copper foil, and by further continuing this hot pressing, the crosslinkable resin is crosslinked, and turns into a crosslinked body having a high heat resistance.

Example 5

A prepreg, a crosslinked resin composite A, and a crosslinked resin composite B were obtained by the same method as in Example 1, except that the 1.7 parts of hexenyl methacrylate was replaced with 3.0 parts of undecenyl acrylate. The evaluation results are shown in Table 1.

Comparative Example 1

A prepreg, a crosslinked resin composite A, and a crosslinked resin composite B were obtained by the same

TABLE 1

| | | Monomer | Chain Transfer Agent | Residual Chain Transfer Agent | Mw | Mw/Mn | Lamination Properties | Peel Strength | tan δ |
|---|---|---|---|---|---|---|---|---|---|
| Example | 1 | norbornene/ tetracyclo- dodecene | hexenyl meth- acrylate (HMA) | A | 22,000 | 1.9 | A | A | A |
| | 2 | norbornene/ tetracyclo- dodecene | pentenyl meth- acrylate (PMA) | A | | 2.0 | A | A | A |
| | 3 | norbornene/ tetracyclo- dodecene | octenyl meth- acrylate (OMA) | A | | 2.1 | A | A | A |
| | 4 | norbornene/ tetracyclo- dodecene | undecenyl meth- acrylate (UMA) | A | | 2.4 | A | B | A |
| | 5 | norbornene/ tetracyclo- dodecene | undecenyl acrylate | A | | 2.4 | A | B | A |
| Comparative Example | 1 | norbornene/ tetracyclo- dodecene | allyl meth- acrylate (AMA) | D | | 3.5 | C | C | C |
| | 2 | norbornene/ tetracyclo- dodecene | 1,5- hexadiene | A | | 2.2 | — | — | — |

Example 2

A prepreg, a crosslinked resin composite A, and a crosslinked resin composite B were obtained by the same method as in Example 1, except that the 1.7 parts of hexenyl methacrylate was replaced with 1.8 parts of pentenyl methacrylate. The evaluation results are shown in Table 1.

Example 3

A prepreg, a crosslinked resin composite A, and a crosslinked resin composite B were obtained by the same method as in Example 1, except that the 1.7 parts of hexenyl methacrylate was replaced with 2.1 parts of octenyl methacrylate. The evaluation results are shown in Table 1.

Example 4

A prepreg, a crosslinked resin composite A, and a crosslinked resin composite B were obtained by the same method as in Example 1, except that the 1.7 parts of hexenyl methacrylate was replaced with 3.0 parts of undecenyl methacrylate. The evaluation results are shown in Table 1.

method as in Example 1, except that the 1.7 parts of hexenyl methacrylate was replaced with 2.6 parts of allyl methacrylate. The evaluation results are shown in Table 1.

Comparative Example 2

A prepreg was obtained by the same method as in Example 1, except that the 1.7 parts of hexenyl methacrylate was replaced with 1.1 parts of 1,5-hexadiene. An attempt was then made using this prepreg to obtain a crosslinked resin composite A in the same manner as in Example 1, but the crosslinking did not sufficiently proceed, which meant that the resin flowed and the crosslinked resin composite A could not be obtained. Since the crosslinked resin composite A could not be evaluated, in Table 1 only the ratio (Mw/Mn) of weight average molecular weight to number average molecular weight is shown.

As shown in Table 1, the polymerizable compositions of the examples which used a chain transfer agent composed of a compound represented by the formula (A):

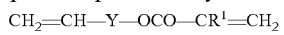

could give a crosslinked resin composite which had no bump and no thin spot and was flat, had good peel strength, and also had a small dielectric loss.

The invention claimed is:

1. A polymerizable composition comprising a norbornene monomer, a metathesis polymerization catalyst, and a chain transfer agent composed of a compound represented by formula (A):

$$CH_2=CH-Y-OCO-CR^1=CH_2$$

wherein Y represents an alkylene group having 3 to 20 carbon atoms, and $R^1$ represents a hydrogen atom or a methyl group.

2. The polymerizable composition according to the claim 1, further comprising a crosslinking agent.

3. A crosslinkable resin obtainable by bulk polymerization of the polymerizable composition according to the claim 2.

4. The crosslinkable resin according to the claim 3, wherein molecular weight distribution (Mw/Mn) represented by a ratio (Mw/Mn) of weight average molecular weight (Mw) to number average molecular weight (Mn) is 3 or less.

5. The crosslinkable resin according to the claim 3, wherein the residual amount of the chain transfer agent is 5% by weight or less on the basis of the added amount of the chain transfer agent.

6. A crosslinkable resin composite obtainable by coating or impregnating the polymerizable composition according to the claim 2 onto or into a support, and then carrying out bulk polymerization.

7. A crosslinked body formable by crosslinking the crosslinkable resin according to the claim 3.

8. A crosslinked resin composite formable by crosslinking a molded article of the crosslinkable resin according to the claim 3 on a support.

9. A crosslinked resin composite formable by crosslinking the crosslinkable resin composite according to the claim 6.

10. The crosslinked resin composite according to the claim 9, wherein the crosslinking is carried out on an added support.

11. A method of manufacturing a crosslinkable resin, comprising the step of carrying out bulk polymerization of the polymerizable composition according to the claim 2.

12. A method of manufacturing a crosslinkable resin composite, comprising the steps of coating or impregnating the polymerizable composition according to the claim 2 onto or into a support, and then carrying out bulk polymerization of the polymerizable composition.

13. A method of manufacturing a crosslinked body, comprising the step of crosslinking the crosslinkable resin according to the claim 3.

14. A method of manufacturing a crosslinked resin composite, comprising the step of crosslinking a molded article of the crosslinkable resin according to the claim 3 on a support.

15. A method of manufacturing a crosslinked resin composite, comprising the step of crosslinking the crosslinkable resin composite according to the claim 6.

16. The method of manufacturing a crosslinked resin composite according to the claim 15, wherein the crosslinking is carried out on an added support.

17. The polymerizable composition according to claim 1, wherein the alkylene group has 4 to 15 carbon atoms.

18. The polymerizable composition according to claim 1, wherein the chain transfer agent is pentenyl (meth)acrylate, hexenyl (meth)acrylate, heptenyl (meth)acrylate, octenyl (meth)acrylate, nonenyl (meth)acrylate, decenyl (meth)acrylate, or undecenyl (meth)acrylate.

* * * * *